United States Patent [19]

Mark et al.

[11] 4,201,878
[45] May 6, 1980

[54] PROCESS FOR PRODUCING BISPHENOLS

[75] Inventors: Victor Mark, Evansville; Lawrence C. Mitchell; Charles V. Hedges, both of Mt. Vernon, all of Ind.

[73] Assignee: General Electric Company, Pittsfield, Mass.

[21] Appl. No.: 876,703

[22] Filed: Feb. 10, 1978

[51] Int. Cl.² .................... C07C 37/00; C07C 39/16
[52] U.S. Cl. .................... 568/723; 568/721; 568/743; 568/744
[58] Field of Search .............. 568/723, 721, 743, 744

[56] References Cited

U.S. PATENT DOCUMENTS

| | | | |
|---|---|---|---|
| 1,977,627 | 10/1934 | Greenhalgh | 568/728 |
| 2,060,716 | 11/1936 | Arvin | 568/723 |
| 2,602,821 | 7/1952 | Luten et al. | 568/723 |
| 2,602,822 | 7/1952 | Schwartzer et al. | 568/723 |
| 2,623,908 | 12/1952 | Stoesser et al. | 568/728 |
| 3,037,946 | 6/1962 | Guest et al. | 568/723 |
| 3,057,928 | 10/1962 | Kobletz et al. | 568/723 |
| 3,065,276 | 11/1962 | Guest et al. | 568/723 |
| 3,242,219 | 5/1966 | Farnham et al. | 568/728 |
| 3,382,283 | 5/1968 | Gundet et al. | 568/723 |
| 4,087,469 | 5/1978 | Gurvich et al. | 568/723 |

Primary Examiner—Norman Morgenstern
Attorney, Agent, or Firm—Morgan, Finnegan, Pine, Foley & Lee

[57] ABSTRACT

Bisphenols substantially free of by-products, are produced rapidly by reacting a phenol and a compound of the formulae:

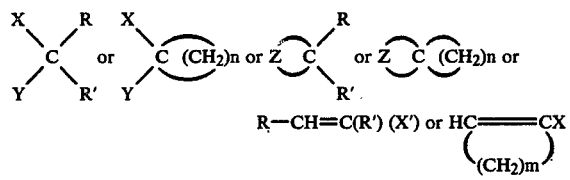

wherein R and R' are hydrogen, lower alkyl or aryl; X is lower alkoxy or the same as X'; Y is chlorine or the same as X; X' is aryloxy; Z is a 1,2- or 1,3-propylenedioxy (that may optionally carry hydroxy, lower alkyl or lower hydroxyalkyl substituents), or arylenedioxy radical; n is integer from three to nine; m is (n−1).

7 Claims, No Drawings

PROCESS FOR PRODUCING BISPHENOLS

The present invention relates to the preparation of highly pure bisphenols.

BACKGROUND OF THE INVENTION

It is well known that bisphenols, such as bisphenol-A, can be obtained by the interaction of phenol with acetone or other ketones in the presence of acidic condensing agents. These processes, however, have yielded products contaminated with a large number of by-products, such as chromans, spiro compounds, linear or cyclic dimers of isopropenylphenols and compounds of more complex structures, which are generally unsuitable for technical operations without extensive and difficult time—and energy—consuming purification steps.

It has now been discovered that excellent yields of highly pure bisphenols can be obtained by substituting for the acetone or other ketone reactant a compound containing as an essential structural feature, an arrangement of carbon and oxygen atoms of any of the following structural formulae:

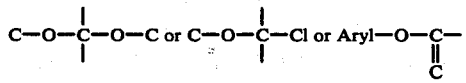

It has been discovered that the reaction is very fast near room temperature (~ 30° C.), and, except for the o,p′ isomer (with phenol as the reactant) only very small amounts of conaminants are formed when "p,p′-bisphenol A" is the desired product. In any event, the by-products, including the o,p′ isomer are easily removed by a simple slurrying of the separated solids with methylene chloride.

DESCRIPTION OF THE INVENTION

According to this invention condensation is effected by acid catalysis between at least equivalent quantities of a phenol, preferably having a reactive hydrogen para to the phenolic hydroxyl, and a compound of any of the following formulae:

I wherein R and R′ are hydrogen, (lower) alkyl or aryl; X is (lower) alkoxy or aryloxy; Y is chlorine or the same as X.

The condensation is effected with facility also with compounds where R and R′ are part of a common cycle, such as in

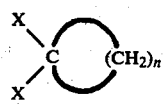

II where n is an integer from 3 to 9, and X is as defined above; or with compounds where X and Y are part of a common cycle, such as in

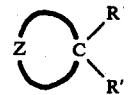

III where Z is a 1,2-propylenedioxy-, or 1,3-propylenedioxy- radical, which may carry (lower)alkyl-, (lower)-hydroxyalkyl- or hydroxyl radical(s); or an arylenedioxy radical; or with compounds represented by the combination of formulae II and III as in IV

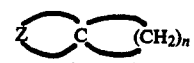

IV or with compounds where either X or Y is represented by unsaturation, such as in V and VI

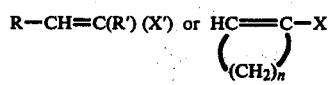

V     VI where X is as previously defined and X′ is aryloxy.

Compounds represented by general formulae I to VI can be considered as masked carbonyls which yield with phenols under acid catalysis the same products as the unmasked carbonyl compounds do without, however, producing the self-condensation products of the latter, which are responsible for the numerous by-products encountered in the reaction of the free carbonyl-bearing reactants. Also, the reactions with phenols of compounds represented by I to VI are much faster than those of the conventional carbonyl compounds. Improvements over the conventional condensation methods are evident also by the color of the products after the removal or neutralization of the acidic catalyst: the crude products obtained from the free carbonyl compounds are yellow to orange, whereas those from the masked carbonyl derivatives are white.

The compounds represented by formulae I to IV can be obtained from carbonyl compounds and alcohols or glycols under acid catalysis; for compounds represented by I when R′ is hydrogen and Y is chlorine, the acid is hydrochloric acid.

Compounds of formulae V and VI can be prepared by several well-known procedures, the most general of which is the dehydrohalogenation of beta-haloethers and the addition of phenols to acetylenes under base catalysis.

It is a preferred feature of the invention to react phenol with 2,2-dimethoxy propane,

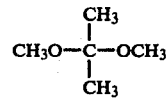

to produce bisphenol A.

Especially favored variants of structures I to VI are those in which X and Y, or X′ are phenoxy radicals, since in their reaction with the corresponding phenols there are no foreign constituents formed in the reaction mixtures. Yields are therefore especially high and the workup and recycle become very simple.

It is therefore a preferred feature to react phenol with isopropenyl phenyl ether

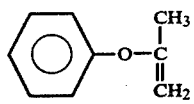

to produce bisphenol A, and with phenyl vinyl ether to produce the bisphenol, VII

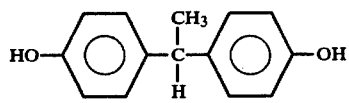

VII

While the reaction in general, can be carried out at temperatures between about 0° C. and 100° C., it is usually carried out at temperatures between 15° C. and 80° C., preferably in the range of from about 20° C. to about 65° C., and especially preferably from about 30° C. to about 50° C. at atmospheric or superatmospheric pressure.

The reaction can be carried out in the absence or in the presence of solvents, such as methylene chloride, 1,2-dichloroethane, benzene, toluene and the like. An especially preferred solvent is the phenol reactant itself, which is thus used in an excess of the stoichiometric proportion. The avoidance of foreign solvents greatly simplifies workup and permits a direct recycling of the phenol.

Any conventional acidic condensing agent can be used, preferably one which is soluble in the phenol employed, e.g., hydrogen chloride, hydrogen bromide, mixtures thereof, sulfuric acid, or phenol-insoluble ones, such as acidic ion exchange resins, and the like. When gaseous hydrogen chloride is used, superatmospheric pressures provide for faster reaction rates.

The condensation reaction can be catalyzed by hydrogen sulfide, mercaptans, thiophenols or compounds with free—SH group. Solid catalysts, such as the acidic ion exchange resins may also be modified by sulfhydryl end groups.

When used herein and in the appended claims, the term "(lower) alkyl" contemplates hydrocarbon chains, straight or branched of from about 1 to about 6 carbon atoms, e.g., methyl ethyl, n-propyl, i-propyl, t-butyl, n-hexyl and the like.

The phenol is employed in from an equivalent amount, e.g., at least 2 moles, and preferably at least 3 moles of phenol per mole of the second reactant. For convenience and economy, the phenol is usually employed in an amount of from 3 to 12 moles per mole of the second reactant, and the excess of phenol can be recovered, usually by distillation, and recycled.

In practice, with a volatile condensing agent, such as HCl, the phenol is melted and the condensing agent is added thereto, suitably in an amount sufficient to maintain the reaction mixture saturated thereto with respect to the condensing agent at a reaction temperature between 15° and 100° C. Superatmospheric pressures are advantageously employed. Either prior to or after adding the acid condensing agent, the second reactant can be mixed in the desired proportions. Condensation is continued preferably until the reaction product typically forms, or consists of, a slurry of crystals comprising the bisphenol in unreacted phenol. The acidic condensation agent can be removed and then the product recovered in a conventional way, e.g., by filtration, centrifugation and the like. Heating the crystalline material which often is a complex of the bisphenol with phenol, in a vacuum will remove unreacted starting materials, and washing with phenol or, preferably, methylene chloride, will remove by-products.

To avoid unnecessary detailed description, conventional techniques for making bisphenols employing phenol and acetone are illustrated in Greenhalgh, U.S. Pat. No. 1,977,627; Stoesser et al, U.S. Pat. No. 2,623,908; and Farnham et al, U.S. Pat. No. 3,242,219, the disclosures of which are incorporated herein by reference.

DESCRIPTION OF THE PREFERRED EMBODIMENTS

The invention is illustrated but not limited by the following examples.

EXAMPLE 1

To a melt of 228 g. (2.42 moles) of phenol saturated with hydrogen chloride at 40.5° C. is added, dropwise, a solution of 31.2 g (0.3 mole) of 2,2-dimethoxypropane (which can be prepared by reacting acetone and methanol by a continuous process and sulfonated polystyrene catalysis) in 30 ml of methylene chloride. After about ⅔ rds. of the solution has been added, the color of the mixture turns to orange. All has been added in one hour and after an additional 2 hours at 35°–39° C., the bisphenol-A adduct precipitates. It is filtered and stripped on a rotary evaporator. The white, solid residue is washed with methylene chloride and this is stripped, too. The product fractions are analyzed by gas phase chromatography which shows the following overall composition:

| Compound | Retention time (min.) | Composition (mole %) |
| --- | --- | --- |
| 2,4'-Isopropylidenediphenol (o,p'-BPA) | 16.52 | 0.8 |
| "Chroman-I"[1] | 17.57 | 5.3 |
| 4,4'-Isopropylidenediphenol (p,p'-BPA) | 17.93 | 93.0 |
| Higher di- and triphenols | 24.92–25.59 | 1.2 |
| p-Cumylphenol (reference) | 14.01 | |

[1] "Chroman-I" has the following structure:

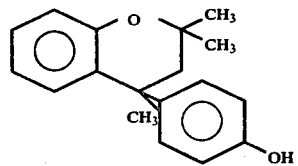

The filtered solids that were washed once with methylene chloride contained 99.77 mole % of p,p'-BPA, 0.19 mole % of o,p'-BPA and 0.04 mole % of higher molecular weight products.

EXAMPLE 2

The procedure of Example 1 was exactly repeated, except that 2,2-dimethoxypropane was replaced with an equivalent amount of acetone (17.4 g, 0.3 mole). The progress of the reaction was followed by gas chromatography, which indicated that following changes in composition:

| Compound | Composition (mole %) | | |
|---|---|---|---|
| | After 1 hr. | After 5 hrs. | After 23 hrs. |
| o,p'-BPA | 29.1 | 17.3 | 8.0 |
| "Chroman-I"[1] | 0.0 | 0.4 | 0.5 |
| p,p'-PBA | 67.6 | 80.1 | 90.1 |
| Higher di- and triphenols | 3.3 | 2.2 | 1.4 |

[1]"Chroman-I" has the following structure:

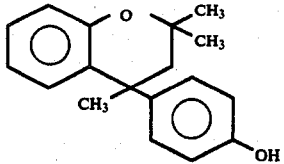

EXAMPLE 3

Into a solution of 697 g of diethyl acetal (5.9 moles) and 3764 g (40 moles) of phenol was introduced at 40° C. with stirring a slow stream of anhydrous hydrogen chloride gas. External cooling was applied to maintain the reaction temperature between 36° and 48° C. After 2.5 hours solids began to separate out from the solution, at which point the introduction of HCl was stopped and the reaction mixture allowed to crystallize at ambient temperature during a 12 hour period. The solids, which were filtered, washed with cyclohexane and air-dried, weighed 890 g and consisted of the 1:1 adduct of 4,4'-ethylidenediphenol and phenol. Separation of the phenol by vacuum distillation at 14 mm pressure left behind the diphenol, that was 98.3% pure by gas chromatographic analysis.

| Compound | Retention time (min.) | Composition (mole %) |
|---|---|---|
| 4,4'-Ethylidenediphenol | 17.32 | 98.3 |
| 2,4'Ethylidenediphenol | 16.32 | 1.7 |
| p-Cumylphenol (reference) | 13.83 | |

One recrystallization from benzene yielded 4,4'-ethylidenediphenol, 99.8% pure by gas chromatography, melting point 123°–125° C.

EXAMPLE 4

The procedure of Example 3 was exactly repeated, except that diethyl acetal was replaced by 780 g of propionaldehyde diethyl acetal. At the end of the reaction, before the separation of solids (while the reaction mixture was still warm), gas chromatographic analysis indicated the presence of 91.5% diphenols and 8.5% of higher molecular weight products. The diphenols had the following composition:

| Compound | Retention time (min.) | Composition (mole %) |
|---|---|---|
| 2,2'-Propylidenediphenol | 15.79 | 5.2 |
| 2,4'-Propylidenediphenol | 16.74 | 28.0 |
| 4,4'-Propylidenediphenol | 17.96 | 66.8 |
| p-Cumylphenol (reference) | 13.97 | |

Stripping of the alcohol in vacuum left behind the liquid reaction mixture, which soon deposited the phenol adduct of 4,4'-propylidenediphenol. Filtration and recrystallization of the white filtrate from benzene yielded 99.9% pure 4,4'-propylidenediphenol, melting point 131°–132° C.

EXAMPLE 5

The procedure of Example 4 was exactly repeated, except that propionaldehyde diethyl acetal was replaced by 342.7 g of propionaldehyde. Gas chromatographic analysis at the end of the reaction indicated the presence of 87.2% diphenols, which had the following composition:

| Compound | Retention time (min.) | Composition (mole %) |
|---|---|---|
| 2,2'-Propylidenediphenol | 15.55 | 13.0 |
| 2,4'-Propylidenediphenol | 16.59 | 27.9 |
| 4,4'-Propylidenediphenol | 17.83 | 60.2 |
| p-Cumylphenol (reference) | 13.82 | |

EXAMPLE 6

The procedure of Example 4 was repeated, except that it was carried out on the one molar scale (based on propionaldehyde diethyl acetal) and that phenol was replaced by the equivalent amount of o-cresol (1081 g, or 10 moles). Gas chromatography indicated the following composition for diphenols at the end of the reaction.

| Compound | Retention time (min.) | Composition (mole %) |
|---|---|---|
| 6,6'-Propylidenedi-o-cresol | 18.21 | 1.5 |
| 4,6'-Propylidenedi-o-cresol | 18.43 | 13.9 |
| 4,4'-Propylidenedi-o-cresol | 19.19 | 84.6 |
| p-Cumylphenol (reference) | 14.13 | |

A small amount (ca. 2.8%) of a higher molecular weight product was also formed in the reaction (retention time: 26.47 min.).

EXAMPLE 7

The procedure of Example 6 was repeated, except that propionaldehyde diethyl acetal was replaced by one mole of 1,2-isopropylidene glycerine. The crude reaction mixture had the following composition:

| Compound | Retention time (min.) | Composition (mole %) |
|---|---|---|
| 4,6'-Isopropylidenedi-o-cresol | 18.12 | 9.0 |
| 4,4'-Isopropylidenedi-o-cresol | 19.90 | 91.0 |
| p-Cumylphenol (reference) | 15.67 | |

EXAMPLE 10

The procedure of Example 6 was repeated on the one mole scale, except that propionaldehyde diethyl acetal was replaced with the equivalent amount of 1,1-dimethoxycyclohexane (144.2 g, one mole; boiling point 54° C. at 15 mm pressure). Gas chromatography showed the following composition at the end of the reaction.

| Compound | Retention time (min.) | Composition (mole %) |
|---|---|---|
| 4,4'-Cyclohexylidenediphenol | 23.35 | 98.7 |
| 2,4'-Cyclohexylidenediphenol | 21.85 | 1.3 |
| p-Cumylphenol | 15.68 | |

Recrystallization from aqueous methanol yielded 99.8% pure 4,4'-diphenol, melting point 188°–189° C.

EXAMPLE 11

The procedure of Example 10 was repeated, except that 1,1-dimethoxycyclohexane was replaced with the cyclic acetal of 1,2-propanediol and cycloheptanone. The reaction preduct was obtained in the following composition, as shown be gas chromatography:

| Compound | Retention time (min.) | Composition (mole %) |
| --- | --- | --- |
| 4,4'-Cycloheptylidenediphenol | 25.35 | 97.8 |
| 2,4'-Cycloheptylidenediphenol | 23.02 | 2.2 |
| p-Cumylphenol (reference) | 16.47 | |

Recrystallization from aqueous methanol yielded 4,4'-cycloheptylidenediphenol in 99.1% purity, melting point 208°–209° C.

EXAMPLE 12

The procedure of Example 1 was repeated, except that 2,2-dimethoxypropane was replaced by 45.0 g (0.3 mole) of 2-phenoxypropene (which can be prepared from phenol and propyne with potassium hydroxide or from sodium phenate and 1,2-dichloropropane). Gas chromatography indicated, at the end of the reaction, the presence of only p,p'-BPA (94.6%), o.p'-BPA (5.4%) and excess phenol.

EXAMPLE 13

Repeating the procedure of Example 4, on the one molar scale, by replacing propionaldehyde diethyl acetal with alphachloropropyl ethyl ether (122.6 g, 1.0 mole) (which is readily obtainable from propionaldehyde, ethyl alcohol and anhydrous hydrogen chloride), yielded a reaction mixture consisting of 93 mole % of diphenols, in which 4,4'-propylidenediphenol predominated (65.0%).

EXAMPLE 14

The process of Example 12 was repeated, except that 2-phenoxypropene was replaced by phenyl vinyl ether, 36.0 g (0.3 mole). At the end of the reaction, gas chromatography indicated the following composition.

| Compound | Retention time (min.) | Composition (mole %) |
| --- | --- | --- |
| 4,4'-Ethylidenediphenol | 17.38 | 98.6 |
| 2,4'-Ethylidenediphenol | 16.37 | 1.4 |
| p-Cumylphenol (reference) | 13.90 | |

EXAMPLE 15

The process of Example 4 was repeated on the molar scale except that propionaldehyde diethyl acetal was replaced with 214.3 g of acetaldehyde diphenyl acetal (obtainable of phenyl vinyl ether and acetic acid via disproportionation). In a very clean reaction 4,4'-ethylidenediphenol (97.6%) and 2,4'-ethylidenediphenol (2.4%) were the only products present in the adduct.

The above description is illustrative. Any variation thereform which conforms to the spirit of the invention is intended to be included within the scope of the claims.

We claim:

1. A process for the production of bisphenols which comprises reacting a phenol having a reactive hydrogen para to the phenolic hydroxyl and a compound of the formula

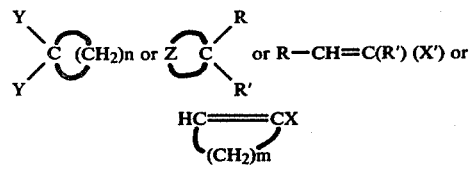

wherein R and R' are hydrogen, lower alkyl or aryl; X is lower alkoxy or the same as X'; Y is chlorine or the same as X; X' is aryloxy; n is integer from three to nine; m is (n-1), or a mixture of such compounds, in the presence of an acidic condensing agent.

2. A process as defined in claim 1 wherein phenol is reacted with isopropenyl phenyl ether to produce bisphenol-A.

3. A process as defined in claim 1 wherein the temperature of reaction is maintained in the range of from about 20° C. to about 65° C.

4. A process as defined in claim 1 wherein the acidic condensing agent is hydrogen chloride.

5. A process as defined in claim 1 which also includes the steps of separating the bisphenol-phenol adduct in solid form and washing the solid product with methylene chloride until substantially free of by-products.

6. A process for the production of bisphenol-A which comprises reacting phenol and isopropenyl phenyl ether in the presence of hydrogen chloride at a temperature of from about 30° to about 50° C.

7. A process as defined in claim 6 which further includes separating the bisphenol-A in solid form as its adduct with phenol from the reaction mixture and washing the solid product with methylene chloride until substantially free of byproducts.